United States Patent [19]

Schär

[11] Patent Number: 4,943,990
[45] Date of Patent: Jul. 24, 1990

[54] THERAPY SIMULATOR

[75] Inventor: Hugo Schär, Flaach, Switzerland

[73] Assignee: BBC Brown Boveri AG, Baden, Switzerland

[21] Appl. No.: 280,499

[22] Filed: Dec. 6, 1988

[30] Foreign Application Priority Data

Dec. 11, 1987 [CH] Switzerland ............ 4846/87

[51] Int. Cl.$^5$ .............................. G21K 1/03
[52] U.S. Cl. ....................... 378/152; 378/65; 378/150
[58] Field of Search .............. 378/151, 150, 152, 65

[56] References Cited

U.S. PATENT DOCUMENTS

| 2,911,537 | 11/1959 | Land . | |
| 4,365,341 | 12/1982 | Lam | 378/65 |
| 4,752,947 | 6/1988 | Telorack | 378/150 |

FOREIGN PATENT DOCUMENTS

| 0187245 | 7/1986 | European Pat. Off. . |
| 2440014 | 5/1980 | France . |
| 2524690 | 10/1983 | France . |

OTHER PUBLICATIONS

Technik der Medizinischen Radiologie, Theodor Laubenberger, 1975, 1986, pp. 42, 122–123, 153, 492–494, 511, 527.

*Primary Examiner*—Craig E. Church
*Attorney, Agent, or Firm*—Burns, Doane, Swecker & Mathis

[57] ABSTRACT

This therapy simulator contains a radiation source (1) in a radiator head. An image acquisition unit (7) is connected to the radiator head and can be swivelled jointly with the latter about a patient's couch (9). At least two diaphragm systems, arranged offset in the direction of the principal axis (2) of the radiation source (1), are arranged in the radiator head. At least one of these diaphragm systems is designed as a depth diaphragm system (4) and at least one other is designed as a measuring diaphragm system (5).

A therapy simulator is to be created on which, together with the setting of the measuring diaphragm, the corresponding depth diaphragm is adjusted automatically. This is achieved by the actuating elements of the at least two diaphragm systems being designed such that the diaphragm systems projected into the image plane of the image acquisition unit (7) move at the same speed.

6 Claims, 2 Drawing Sheets

THERAPY SIMULATOR

BACKGROUND OF THE INVENTION

1. Field of the Invention

The invention is based on a therapy simulator having a radiator head containing a radiation source, having an image acquisition unit, connected to the said radiator head and able to swivel jointly with it, and having an adjustable patient's couch, which can be moved between radiator head and image acquisition unit. In particular, it relates to a therapy simulator having at least two diaphragm systems, arranged in the radiator head offset in the direction of the principal axis of the radiation source, of which systems at least a first is designed as a depth diaphragm system and at least a second is designed as a measuring diaphragm system.

2. Discussion of Background

A therapy simulator of the generic type is known from the book "Technik der medizinischen Radiologie" (Medical Radiology Technology) by Theodor Laubenberger (Deutscher Aerzte-Verlag GmbH, Cologne, 4th edition 1986). In the case of this therapy simulator, all settings are displayed on a control console and the corresponding data, such as position, size of the irradiation field and angular setting, are logged. At the same time, X-ray pictures of the irradiation field and of the surrounding field are taken. The depth diaphragm system and the measuring diaphragm system are remotely controlled independently of each other, so how long the patient to be examined is exposed to the X-radiation and how quickly healthy parts of the body are protected against the radiation depends on the skill of the operator.

SUMMARY OF THE INVENTION

Accordingly, one object of this invention, as defined in the claims, is to provide a novel therapy simulator on which, together with the setting of the measuring diaphragm, the corresponding depth diaphragm is automatically adjusted, as a result of which the radiation load for the patient is restricted to the absolute necessary.

The advantages achieved by the invention are essentially to be seen in that the operation of the therapy simulator is substantially simplified by the linking of the movement of the measuring diaphragm to that of the corresponding depth diaphragm. The radiator head may be of a very compact design and, as many identical parts can be used, simple stocking of spare parts is also possible. Furthermore, the moving parts of the diaphragm systems are subjected to only very low wear as the said parts cannot be twisted in guiding parts.

Further developments of the invention are covered by the dependent claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
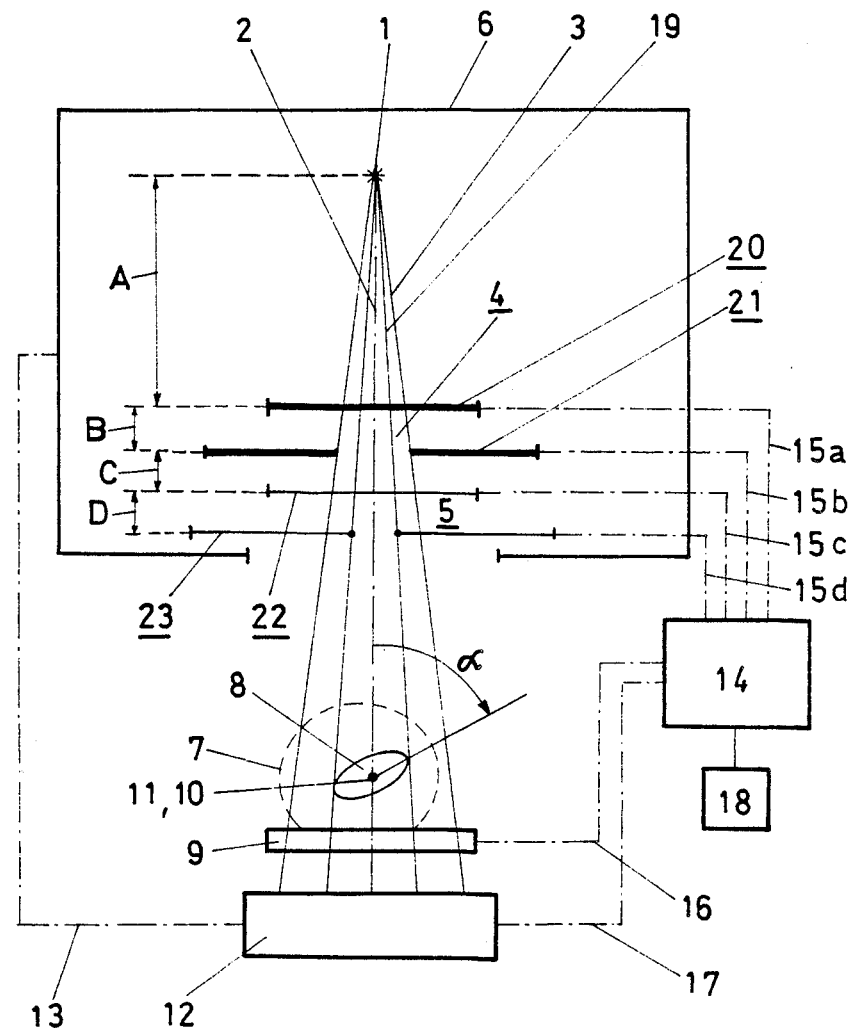
FIG. 1 shows a basic diagram of a therapy simulator according to the invention.

Referring now to the drawings, wherein like reference numerals designate identical or corresponding parts throughout the several views, in FIG. 1 a therapy simulator according to the invention is shown. Casing parts of the simulator are only indicated; the respective sizes in this basic diagram are not shown to scale. An X-ray tube, the radiation of which forms a radiation cone 3 in the direction of a principal axis 2, may be provided as radiation source 1. The radiation source 1 is arranged together with a depth diaphragm system 4 and a measuring diaphragm system 5 in a radiator head 6, which bears the radiation source 1 and the diaphragm systems and at the same time screens off stray radiation effects. The radiation cone 3 emanating from the radiator head 6 penetrates a patient, the cross-section of which is indicated by the dashed line 7, with a tumor 8. The patient is positioned on an adjustable patient's couch 9. Often, the patient is positioned such that the center 10 of the tumor 8 lies on the principal axis 2 and at the same time on the swivel axis 11 of the therapy simulator, which axis extends perpendicular to the plane of the figure. Other types of position are possible, according to the particular therapy objectives of the physician carrying out the treatment. Underneath the radiotranslucent patient's couch 9 is arranged an image acquisition unit 12. The radiator head 6 and the image acquisition unit 12 are mutually displaceable along the principal axis 2 and are held by the frame of the therapy simulator, which frame is merely indicated by a line of effect 13 and may take the form of a welded or cast structure; in addition, they may be swivelled jointly, motor-driven, about the swivel axis 11 in both directions by a swivel angle $\alpha$. The swivelling range of the therapy simulator is adapted to that of an associated radiotherapy unit. At the same time, if necessary, the patient's couch 9 can also be moved. The control of all movements and their coordination takes place in a central control unit 14.

It is indicated by the lines of effect 15a, 15b, 15c and 15d that the central control unit 14 acts via actuating elements on the diaphragm systems 4, 5, and that, conversely, position messages from the diaphragm systems 4, 5 come back into the control unit 14. The line of effect 16 indicates the actuation possibility and the position message for the patient's couch 9. The corresponding connection to a drive system responsible for the swivelling by the swivel angle $\alpha$ is not drawn in. The line of effect 17 indicates the possibility that, coordinated with the other return messages, image information flows back into the control unit 14 and can be processed there for joint storage with the position messages in a memory 18 connected to the control unit 14. The image information may also be displayed on display devices. The movement data and position messages are then transmitted either online or by means of a data carrier into a memory of the associated radiotherapy unit.

A radiation cone 19, as is defined by the position of the measuring diaphragm system 5 in the plane represented, determines the irradiation field in the associated radio-therapy unit. If the therapy simulator is then swivelled by the swivel angle $\alpha$ and at the same time the measuring diaphragm system 5 is made to follow it in such a way that the tumor 8 is always just still bounded, in the case shown in the diagram, the radiation cone 19 becomes more and more sharp and the irradiation field in this plane thereby becomes smaller.

A first diaphragm pair 20 of the depth diaphragm system 4 is arranged at the distance A from the radiation source 1 and a second diaphragm pair 21 is arranged at the distance A+B. The first diaphragm pair 20 and the second diaphragm pair 21 of the depth diaphragm system 4 are arranged turned through 90° with respect to each other. At the distance A+B+C from the radiation source 1, a first diaphragm pair 22 of the measuring diaphragm system 5 is arranged turned through 90° with respect to the diaphragm pair 21. A second diaphragm pair 23 of the measuring diaphragm system 5 is arranged at the distance A+B+C+D from the radiation source 1, it is turned through 90° with respect to the diaphragm pair 22. The distances B, C and D are chosen here to be equal in each case, as in this way a compact design of the radiator head 6 can be realized, but in other embodiments they may also be of different sizes. In addition, it is possible to align the first diaphragm pair 22 and the measuring diaphragm system 5 the same as the diaphragm pair 21 of the depth diaphragm system 4.

The diaphragm pair 20 is moved by actuating elements, which are designed such that the speed of movement of the diaphragm pair 20 is proportional to the distance A from the radiation source 1. The actuating elements for the diaphragm pair 21 move the latter at a speed proportional to the distance A+B, while the diaphragm pair 22 is moved proportionally to the distance A+B+C and the diaphragm pair 23 is moved proportionally to the distance A+B+C+D. This speed distribution proportional to the distance of the respective diaphragm pair from the radiation source 1 has the advantage that the diaphragm systems 4, 5 projected into the image plane of the image acquisition unit 12 can move there at the same speed.

Figure 2:
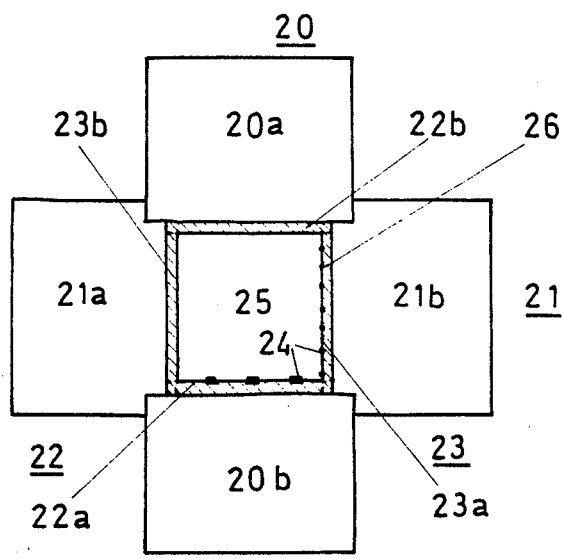
FIG. 2 shows a plan view of the diaphragm systems.

Each of the diaphragm pairs 20, 21, 22 and 23 consists of two mutually opposite diaphragms, as evident from FIG. 2.

In this arrangement, the diaphragm pair 20 is assigned the diaphragms 20a and 20b, which consist of lead plates, similarly the diaphragm pair 21 is assigned the diaphragms 21a and 22b, likewise of lead. The diaphragm pair 22 is assigned the diaphragms 22a and 22b, consisting of tungsten wire or molybdenum wire, and the diaphragm pair 23 is assigned the corresponding diaphragms 23a and 23b. The diaphragms 22a and 23a are unmistakeably marked on radiopaque shaped pieces 24 fastened to them. An irradiation field 25 is framed by the diaphragms 22a, b and 23a, b. A border zone 26, represented by shading, is formed between the diaphragms 22a, b, 23a, b and the diaphragms 20a, b and 21a, b.

Each of the diaphragms 20a, b, 21a, b, 22a, b and 23a, b is driven individually, for example by a direct-current motor and, should it be necessary, each diaphragm can also be moved individually. As a rule, however, the diaphragms 20a, b and 21a, b of the depth diaphragm system 4 are linked by the associated diaphragms 22b, a and 23b, a. This linking is ensured by the central control unit 14. Due to this linking, once set, the width of the border zone 26 is maintained in all diaphragm positions and does not have to be readjusted manually each time. An equivalent linking could also be achieved by interposing a differential gear in each case between the mutually assigned diaphragms.

Figure 3:
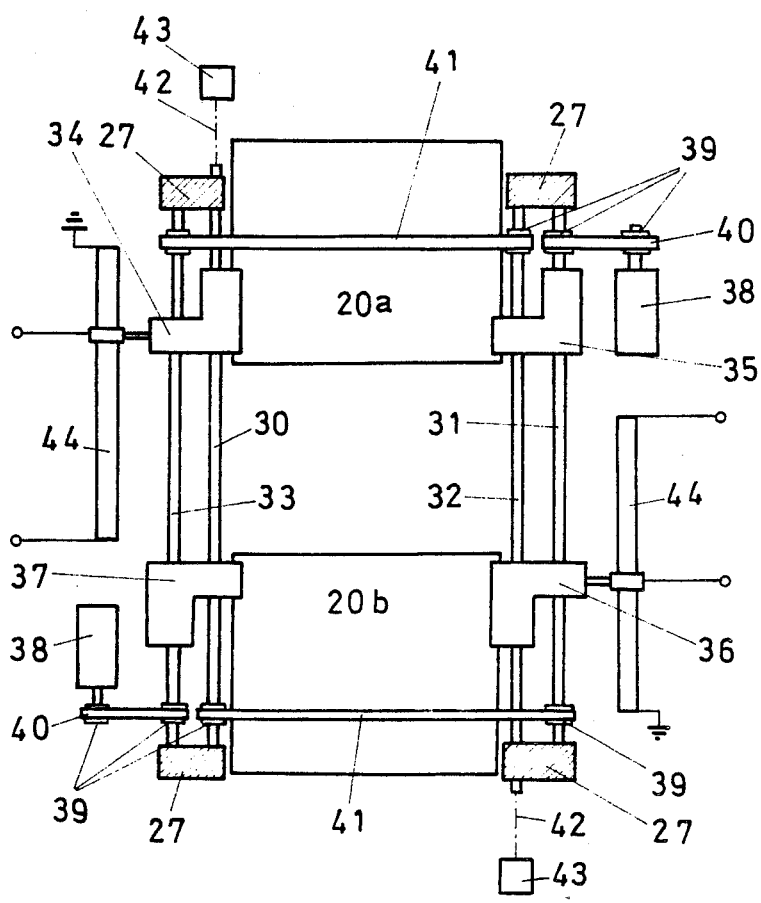
FIG. 3 shows a basic diagram of a diaphragm pair.

In FIG. 3, the diaphragm pair 20 of the depth diaphragm system 4 is represented in somewhat more detail. Spindles 30, 31, 32 and 33, which are mounted rotatably in bearings 27 connected fixedly to the radiator head 6 and which lie parallel in a plane, bear holders 34, 35, 36 and 37, which hold the diaphragms 20a and 20b in pairs. In this arrangement, the diaphragm 20a is held by the holders 34 and 35 and moved by the spindles 30 and 31. It suffices here merely to drive the spindle 31 with a drive 38 via pinion 39 and a toothed belt 40, the second spindle 30 is mechanically linked by a pinion 39 and a second toothed belt 41. The diaphragm 20b is held by the holders 36 and 37 and moved by the spindles 32 and 33, which are driven by similar actuating elements as the diaphragm 20a. Into the holder 34 there is pressed a threaded sleeve, into which the spindle 30 engages; in addition, a second borehole is provided, through which the spindle 33 slides. The other holders 35, 36 and 37 are correspondingly designed. Due to the dual function of the spindles 30, 31, 32, 33 as actuating elements and at the same time as guiding elements, the diaphragm pair 20 is given a great stability and the holders 34, 35, 36, 37 cannot twist, consequently the wear on the sliding parts in engagement with one another of the diaphragm pair 20 is extremely low.

The pitch of the spindles 30, 31, 32 and 33 and that in their counterpieces has been chosen proportional to the distance A from the radiation source 1. The corresponding parts of the diaphragm pair 21 have a pitch proportional to the distance A+B. The corresponding parts of the diaphragm pairs 22 and 23 have pitches proportional to the distances A+B+C and A+B+C+D, respectively. The spindles 30 and 31 have the same axial distance from each other as the spindles 32 and 33.

The respective position of the diaphragm systems 4, 5 can be monitored by means of sensors. The position of the diaphragms can be detected particularly precisely by two mutually independent sensors. One of these sensors is designed as an angle of rotation pickup 43, linked to the respective driving spindles 30, 32, as indicated by a line of effect 42, another of these sensors is designed as a potentiometer 44 detecting the overall travel of the respective diaphragm. In the central control unit 14, the position data of both sensors 43, 44 are compared and, if in agreement, stored in the memory 18. In the event that one sensor is faulty, the control unit 14 indicates this and the damage must be repaired, since wrongly recorded data could endanger the patient concerned. As a rule, however, it should suffice to monitor precisely only the position of the diaphragm of the measuring diaphragm system 5, as it is after all these with which the precise irradiation field is delimited.

The operating principle of this therapy simulator is to be briefly explained. It is used for the planning of tumor irradiation operations on a patient positioned appropriately for therapy on the patient's couch 9. The geometric relationships of the simulator are matched to those of the actual radiotherapy unit, by radiator head 6 and image acquisition unit 12 being displaced with respect to each other. In the event that these possibilities, based on the mechanical design, do not suffice, the data stored in the memory 18 can be adapted with the aid of the central control unit 14, to the respective radiotherapy unit. The patient is, for example, positioned on the patient's couch 9 such that the center 10 of his tumor 8 lies on the principal axis 2 of the radiation source 1 and at the same time on the swivel axis 11 about which radiator head 6 and image acquisition unit 12 jointly swivel.

During the swivelling movement, X-ray pictures of the tumor 8 are taken and, by means of the measuring diaphragm system 5, the irradiation field 25 which is later to be irradiated in the actual radiotherapy unit is defined dependently on the swivel angle α. In this case it is very advantageous if the measuring diaphragm is linked to the corresponding depth diaphragm as, for example when reducing the irradiation field 25, the depth diaphragm moves inwards at the same time as the movement of the measuring diaphragm, and immediately protects healthy tissue from the X-radiation. The operation of the therapy simulator is thereby simplified and the protection of healthy body tissue is improved. Various linking possibilities of the various diaphragm systems are conceivable, which can be chosen depending on the size and position of the tumor in the body of the patient. An operation without this linking is likewise possible, should this be necessary for therapeutic reasons.

In the case of the exemplary embodiment, the diaphragms are moved by direct-current motors with gears connected ahead of them and the drive energy is transmitted by means of toothed belts. When end positions are reached, a slipping clutch comes into effect. Other drives, for example linear motors or speed-controlled drives are likewise conceivable, as are other power transmissions, such as for example rack and worm-pinion gears modified to the diaphragm movements according to the requirements pointed out.

The image sections determined by the diaphragms do not always have to be rectangular. It is quite conceivable also to use diaphragms which are better matched or can be better matched to the shape of the tumor to be treated. In addition, it is not necessary to center the tumor 8 in the irradiation field 25, giving the physician carrying out the treatment comparatively wide freedom in planning the tumor irradiation operations.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A therapy simulator comprising:
   a radiator head having a radiation source,
   an image acquisition unit connected to said radiator head having means for swiveling said image acquisition unit along with said radiator head around a swivel axis,
   an adjustable patient's couch movable between said radiator head and said image acquisition unit,
   first and second diaphragm systems arranged in said radiator head such that said first and second diaphragm systems are offset in the direction of a principal axis of said radiation source, said first and second diaphragm systems having actuating elements capable of moving said first and second diaphragm systems at substantially the same speed, wherein
   at least one of said first and second diaphragm systems is comprised of at least four diaphragms situated opposite each other to form two diaphragm pairs,
   each of said two diaphragm pairs being arranged at substantially a 90° angle with respect to each other and in substantially adjacent planes,
   said first diaphragm system having at least one diaphragm linkable to at least one diaphragm of said second diaphragm system, and
   said linked diaphragms jointly movable in the same direction,
   each of said four diaphragms being movable by means of at least two corresponding driving spindles, each of said at least two spindles being threadably engaged in a diaphragm holder, each of said at least two spindles having a thread pitch that is proportional to the distance of the corresponding diaphragm from said radiation source, and
   each of said four diaphragms being provided with said at least two driving spindles such that at least four driving spindles are provided for each diaphragm pair, said at least four driving spindles being positioned parallel to one another in a plane, and each of said four diaphragms having at least two diaphragm holders being guided by said at least two driving spindles.

2. The therapy simulator as claimed in claim 1, having a second diaphragm system comprised of a plurality of wires, wherein a plurality of radiopaque shaped pieces are attached to at least one of said plurality of wires.

3. The therapy simulator as claimed in claim 1, wherein each of said first and second diaphragm systems is comprised of four diaphragms opposite each other to form diaphragm pairs,
   said diaphragm pairs of said first diaphragm system being arranged at substantially a 90° angle with respect to each other and in substantially adjacent planes,
   said diaphragm pairs of said second diaphragm system being arranged at substantially a 90° angle with respect to each other and in substantially adjacent planes, a diaphragm pair of the first diaphragm system being arranged at substantially a 90° angle with respect to a diaphragm pair of said second diaphragm system and in a substantially adjacent plane.

4. The therapy simulator as claimed in claim 1, wherein said at least two driving spindles for each of said four diaphragms are separated by a predetermined distance.

5. The therapy simulator as claimed in claim 4, wherein said second diaphragm system is comprised of said four diaphragms in said two diaphragm pairs and includes means for detecting and storing the position of said four diaphragms in said tow diaphragm pairs in relation to said swiveling movement of said radiator head and said image acquisition unit.

6. The therapy simulator as claimed in claim 5, wherein said second diaphragm system includes for each of said four diaphragms a first sensor and a second sensor, said first and second sensors having means for obtaining position data for each of said four diaphragms of said two diaphragm pairs of the second diaphragm system, said first sensor capable of measuring an angle of rotation of one of said at least two driving spindles, said second sensor comprised of a potentiometer and capable of detecting an overall travel of one of each of said four diaphragms, said position data from said first and second sensors being compared with one another in a control unit.

* * * * *